United States Patent
Choi

(10) Patent No.: US 9,285,309 B2
(45) Date of Patent: Mar. 15, 2016

(54) IMAGE FUSION METHOD AND APPARATUS USING MULTI-SPECTRAL FILTER ARRAY SENSOR

(71) Applicant: HANWHA TECHWIN CO., LTD., Changwon-si (KR)

(72) Inventor: Eun-Cheol Choi, Changwon (KR)

(73) Assignee: Hanwha Techwin Co., Ltd., Changwon-si (KR)

( * ) Notice: Subject to any disclaimer, the term of this patent is extended or adjusted under 35 U.S.C. 154(b) by 360 days.

(21) Appl. No.: 13/953,895

(22) Filed: Jul. 30, 2013

(65) Prior Publication Data

US 2014/0218538 A1  Aug. 7, 2014

(30) Foreign Application Priority Data

Feb. 4, 2013 (KR) .................. 10-2013-0012607

(51) Int. Cl.
*G01N 21/359* (2014.01)
*H04N 5/33* (2006.01)
*H04N 9/07* (2006.01)

(52) U.S. Cl.
CPC ............ *G01N 21/359* (2013.01); *H04N 5/332* (2013.01); *H04N 9/07* (2013.01)

(58) Field of Classification Search
CPC .......................... H04N 5/332; H04N 5/3537
See application file for complete search history.

(56) References Cited

U.S. PATENT DOCUMENTS

| 6,211,521 B1 | 4/2001 | Bawolek et al. |
| 7,956,325 B2 | 6/2011 | Tanimoto |
| 2004/0141659 A1 | 7/2004 | Zhang |
| 2010/0124373 A1 | 5/2010 | Yoo et al. |

FOREIGN PATENT DOCUMENTS

KR  1020100055067 A  5/2010

OTHER PUBLICATIONS

Schaul, Lex, Clément Fredembach, and Sabine Süsstrunk. "Color image dehazing using the near-infrared." Proc. IEEE International Conference on Image Processing (ICIP). No. LCAV-CONF-2009-026. 2009.*

Li, Shutao, and Xudong Kang. "Fast multi-exposure image fusion with median filter and recursive filter." Consumer Electronics, IEEE Transactions on 58.2 (2012): 626-632.*

Varjo, Sami, Jari Hannuksela, and Sakari Alenius. "Comparison of near infrared and visible image fusion methods." Proc. International Workshop on Applications, Systems and Services for Camera Phone Sensing. 2011.*

* cited by examiner

*Primary Examiner* — Sath V Perungavoor
*Assistant Examiner* — Clifford Hilaire
(74) *Attorney, Agent, or Firm* — Sughrue Mion, PLLC

(57) ABSTRACT

Provided is an image fusion apparatus using a multi-spectral filter array sensor, the image fusion apparatus including a separation unit configured to separate an input image input through the multi-spectral filter array sensor into an RGB image and a near infrared (NIR) image, a color reconstruction unit configured to extract an RGB image in a visible band by removing an NIR value incident together with R, G and B values through the multi-spectral filter array sensor from the R, G and B values, and an image fusion unit configured to fuse the RGB image in the visible band with the NIR image, in which a fusion rate of the RGB image and the NIR image is based on a size of each of the R, G and B values of the RGB image in the visible band.

11 Claims, 4 Drawing Sheets

IMAGE FUSION METHOD AND APPARATUS USING MULTI-SPECTRAL FILTER ARRAY SENSOR

CROSS-REFERENCE TO RELATED PATENT APPLICATION

This application claims priority from Korean Patent Application No. 10-2013-0012607, filed on Feb. 4, 2013, in the Korean Intellectual Property Office, the disclosure of which is incorporated herein in its entirety by reference.

BACKGROUND

1. Field

Apparatuses and methods consistent with exemplary embodiments relate to image processing, and more particularly, to fusing an RGB image with a near infrared (NIR) (or black/white) image from among images obtained using a multi-spectral filter array.

2. Description of the Related Art

To obtain an image in a visible band and an NIR image in an invisible band at the same time, the images in respective channels may be simultaneously obtained using a multi-spectral filter array as shown in FIG. 1.

Thereafter, an RGB image and an NIR image are separated from the obtained images and processed, and then, these images are finally fused together to improve image sensitivity.

SUMMARY

One or more exemplary embodiments are provided to address a problem of a related art in which chroma is damaged because in a process of fusing an RGB image and an NIR image, the fusion is performed without considering a size of each of R, G, and B values in the visible RGB image.

According to an aspect of an exemplary embodiment, there is provided an image fusion apparatus using a multi-spectral filter array sensor, the image fusion apparatus including: a separation unit configured to separate an input image input through the multi-spectral filter array sensor into an RGB image and a near infrared (NIR) image; a color reconstruction unit configured to extract an RGB image in a visible band by removing an NIR value incident together with R, G and B values through the multi-spectral filter array sensor from the R, G and B values; and an image fusion unit configured to fuse the RGB image in the visible band with the NIR image, in which a fusion rate of the RGB image and the NIR image is based on a size of each of the R, G and B values of the RGB image in the visible band.

According to an aspect of another exemplary embodiment, there is provided an image fusion method using a multi-spectral filter array sensor, the image fusion method including: extracting an RGB image in a visible band from an RGB image input through the multi-spectral filter array sensor; receiving input of an NIR image through an NIR filter of the multi-spectral filter array sensor; calculating a size of each of R, G and B values of the RGB image in the visible band; and fusing the RGB image in the visible band with the NIR image according to the calculated size of each of R, G, and B pixels.

In the fusing the RGB image in the visible band with the NIR image, a fusion rate of the two images may be adjusted according to local or global characteristics of the input image.

BRIEF DESCRIPTION OF THE DRAWINGS

The above and other aspects will become more apparent by describing in detail exemplary embodiments with reference to the attached drawings, in which.

DETAILED DESCRIPTION OF THE EXEMPLARY EMBODIMENTS

The terminology used herein is for the purpose of describing embodiments and is not intended to be limiting of the present inventive concept. As used herein, the singular forms may include the plural forms as well, unless the context clearly indicates otherwise. It will be further understood that the terms "comprises" and/or "has" when used in this specification, specify the presence of stated component, step, operation and/or element but do not preclude the presence or addition of one or more other components, steps, operations and/or elements.

The terms used herein, including technical and scientific terms, have the same meanings as terms that are generally understood by those skilled in the art, as long as the terms are differently defined. It should be understood that terms defined in a generally-used dictionary have meanings coinciding with those of terms in the related technology. As long as the terms are not defined obviously, they are not ideally or excessively analyzed as formal meanings.

Figure 1:
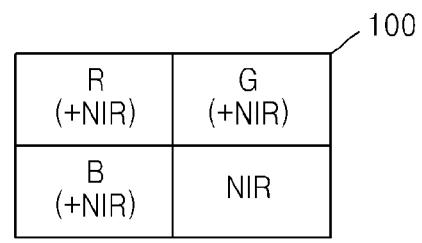
FIG. 1 illustrates an example of a multi-spectral filter array sensor.

Generally, an intensity-hue-saturation (IHS) based image fusion method has been widely used in which an RGB image and a near infrared (NIR) image are separated from a multi-spectral image including R, G, B and NIR channels obtained using a multi-spectral filter array sensor as shown in FIG. 1, processed, and then, fused together.

In the IHS based image fusion method, a color image in a color domain is color-converted, and then, I (Intensity) corresponding to spatial information and H (Hue) and S (Saturation) corresponding to spectral information are separated as below.

$$\begin{pmatrix} I \\ v_1 \\ v_2 \end{pmatrix} = \begin{pmatrix} \frac{1}{3} & \frac{1}{3} & \frac{1}{3} \\ \frac{1}{\sqrt{6}} & \frac{1}{\sqrt{6}} & -\frac{2}{\sqrt{3}} \\ \frac{1}{\sqrt{2}} & -\frac{1}{\sqrt{2}} & 0 \end{pmatrix} \cdot \begin{pmatrix} R \\ G \\ B \end{pmatrix} \quad (1)$$

$$H = \tan^{-1}\left(\frac{v_2}{v_1}\right), S = \sqrt{v_1^2 + v_2^2}$$

The I, H and S components obtained using Equation 1 are converted into an RGB color domain, and then, I (Intensity) components of R, G and B are substituted with an NIR image (or black/white image). The spatial information and the spectral information substituted with the NIR image are substituted with the RGB color domain, thereby obtaining a finally fused image.

The IHS based image fusion method may have problems in terms of loss of details of information and chroma degradation if the spatial information and the spectral information are more insufficient than the I (Intensity) information. In the related art IHS based method compensation information mainly includes NIR information, and thus, the foregoing problems occur.

As described above, FIG. 1 illustrates an example of a multi-spectral filter array sensor 100.

According to an exemplary embodiment, NIR information incident together with RGB pixel value obtained using the multi-spectral filter array sensor 100 is subtracted using NIR pixel values, thereby avoiding use of an IR cutoff filter (IRCF).

More specifically, a wavelength band range of respective channels $R_{all}$, $G_{all}$, $B_{all}$ and $N_{all}$ obtained using the multi-spectral filter array sensor 100 as in Equations 2(a)-2(d) is about 400 nm to about 1100 nm, in which NIR information is also obtained as well as visible band information.

$$R_{all} = R_{vis} + R_{nir} \tag{2(a)}$$

$$G_{all} = G_{vis} + G_{nir} \tag{2(b)}$$

$$B_{all} = B_{vis} + B_{nir} \tag{2(c)}$$

$$N_{all} = N_{vis} + N_{nir} \tag{2(d)}$$

Therefore, by removing the NIR value or information ($R_{nir}$, $G_{nir}$, $B_{nir}$) from the respective color channels $R_{all}$, $G_{all}$ and $B_{all}$, the color of only a visible band may be obtained.

The multi-spectral filter array sensor 100 is a sensor arranged in a form shown in FIG. 1. The multi-spectral filter array sensor 100 includes a color filter which passes light components of a visible band ranging from 400 nm to 700 nm, such as RGB, and an NIR filter which passes light components of a near-infrared zone of 700 nm to 1100 nm in an invisible band.

The multi-spectral filter array sensor 100 outputs an image by using pixels corresponding to R, G and B in a day mode and outputs a black/white image by using pixels corresponding to NIR in a night mode to improve image sensitivity.

According to an exemplary embodiment, to address the related art IHS based image fusion method, NIR pixel values are fused in proportion to R, G and B pixel values.

Figure 2:
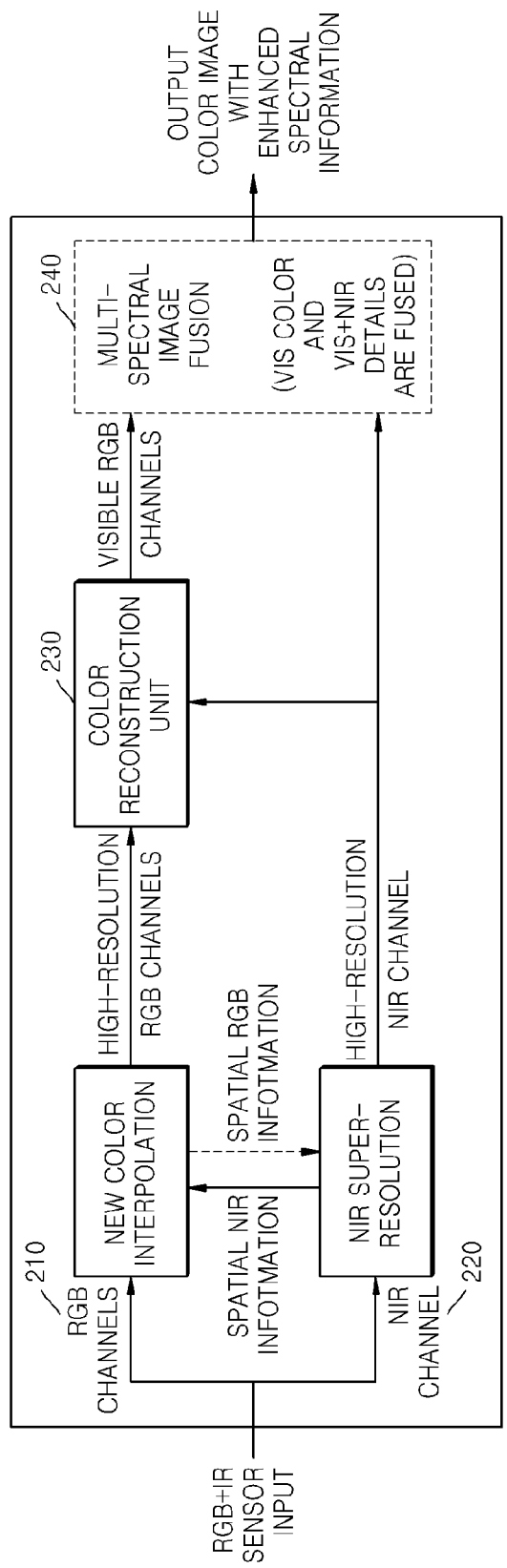
FIG. 2 is a block diagram of an image fusion system using a multi-spectral filter array sensor, according to an exemplary embodiment.

FIG. 2 is a block diagram of an image fusion system using a multi-spectral filter array sensor, according to an exemplary embodiment.

An example of an image fusion system using a multi-spectral filter array sensor may include a camera system which may be an image capturing system such as a digital camera, a camcorder, or a surveillance camera. The camera system may be mounted on a computer, a personal digital assistant (PDA), a portable multimedia player (PMP), a smart phone, a tablet personal computer (PC), or a mobile phone, according to a further exemplary embodiment.

An input signal such as light that is input through the multi-spectral filter array sensor is separated into an RGB channel image 210 and an NIR channel image 220 by a separation unit 200. A color reconstruction unit 230 performs color reconstruction on respective color channels $R_{all}$, $G_{all}$, and $B_{all}$ of RGB channels based on Equations 2(a)-2(d) by using NIR channel information. Thereafter, an image fusion unit 240 fuses an RGB image in the visible band extracted from the respective color channels $R_{all}$, $G_{all}$ and $B_{all}$ together with the NIR image.

Figure 3:
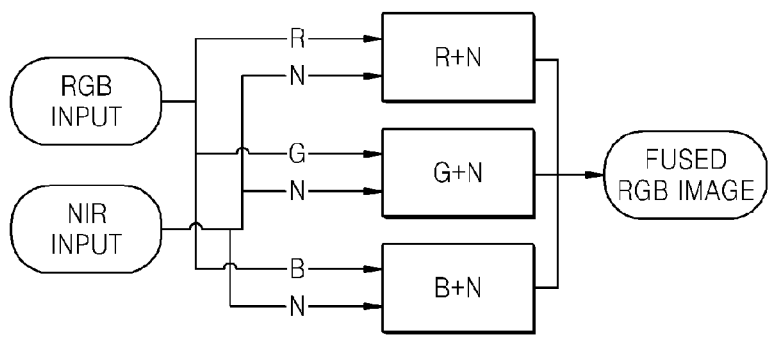
FIG. 3 illustrates an example of the concept of image fusion.

FIG. 3 illustrates an example of the concept of image fusion.

Generally, when an RGB image and an NIR image are fused together, N pixels are added to R, G, and B pixels, respectively, as shown in FIG. 3. In this case, the same N pixel is added to the R, G, and B pixels without considering the portion of R, G and B pixels in the RGB image, such that differences among the original R, G and B pixels are reduced, and thus, image chroma is degraded.

Figure 4:
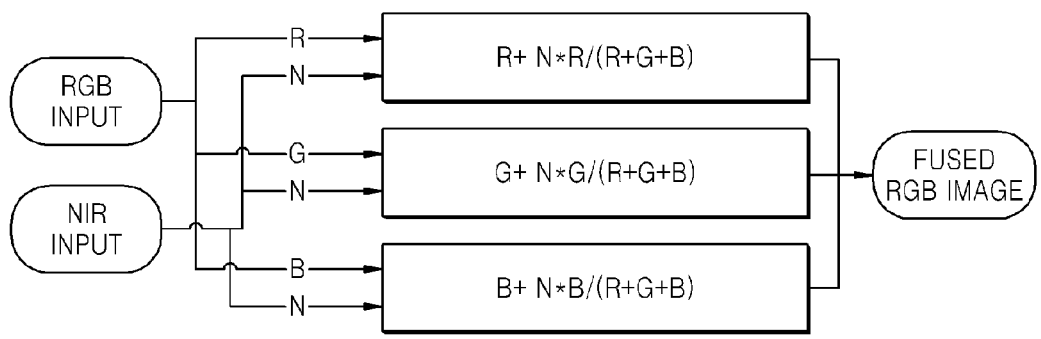
FIG. 4 illustrates an example of an image fusion method according to an exemplary embodiment.

FIG. 4 illustrates an example of an image fusion method according to an exemplary embodiment.

In the present embodiment, to address the problem that occurs when the RGB image and the NIR image are fused together in the manner shown in FIG. 3, N pixels are added based on a size ratio of the R, G and B pixel values. More specifically, in the present embodiment, an RGB image and an NIR image are fused as follows:

$$\begin{pmatrix} R' \\ G' \\ B' \end{pmatrix} = \begin{pmatrix} 1+k & 0 & 0 \\ 0 & 1+k & 0 \\ 0 & 0 & 1+k \end{pmatrix} \cdot \begin{pmatrix} R \\ G \\ B \end{pmatrix}, \tag{3}$$

where $k = \dfrac{3N}{R+G+B}$.

According to an exemplary embodiment, when the RGB image and the NIR image are fused together using Equation 3, a brightness I' (Intensity) of the resulting fused image is given by:

$$I' = (R'+G'+B')/3 = I+N \tag{4},$$

where I indicates a brightness of the RGB image in which I=(R+G+B)/3, and N indicates a brightness of the NIR image.

By fusing the RGB image together with the NIR image according to the present embodiment, the same brightness as that of an image fused using the related art IHS based method may be obtained, and at the same time, the original image chroma may also be maintained.

Figure 5:
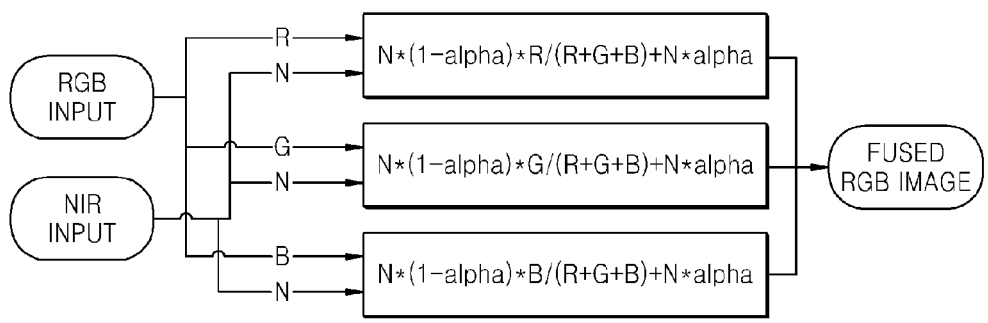
FIG. 5 illustrates an example of fusion between an RGB image and a near infrared (NIR) image, according to another exemplary embodiment.
Figure 6:
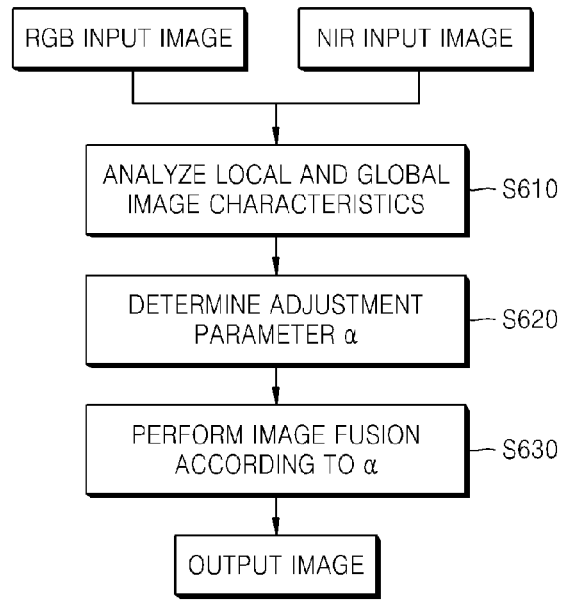
FIG. 6 is a flowchart illustrating a process of fusing an RGB image with an NIR image while adjusting brightness and color, according to an exemplary embodiment.

FIG. 5 illustrates an example of fusion between an RGB image and an NIR image according to another exemplary embodiment, and FIG. 6 is a flowchart illustrating a process of fusing an RGB image with an NIR image while adjusting brightness and color according to an exemplary embodiment.

According to the other embodiment, when the RGB image and the NIR image are fused together, brightness and color may be adjusted according to image characteristics or an image application field.

Specifically, the RGB image and the NIR image may be fused together as given by:

$$R' = N \times (1-\alpha) \times R/(R+G+B) + N \times \alpha \tag{5(a)}$$

$$G' = N \times (1-\alpha) \times G/(R+G+B) + N \times \alpha \tag{5(b)}$$

$$B' = N \times (1-\alpha) \times B/(R+G+B) + N \times \alpha \tag{5(c)},$$

where $0 \leq \alpha \leq 1$.

In Equations 5(a)-5(c), in the day mode, 'α' is reduced to output an image by mainly using values corresponding to R, G and B, and in the night mode, 'α' is increased to output a black/white image by mainly using pixel information corresponding to NIR, thereby improving image sensitivity.

In addition, local or global characteristics of an image may be analyzed to adjust 'α' to adjust color or brightness of the image.

In operation S610, an RGB input image and an NIR input image are input, and image characteristics are analyzed. In this case, the image characteristics may be analyzed locally or globally. The alpha ('α') value may be set based on a brightness statistic value of a particular region in the image, or may be set to a constant value. A user may also set the alpha ('α') value according to user desired output image conditions. For example, if much NIR image information is required, the alpha ('α') value may be set large; and if much RGB image information is required, the alpha ('α') value may be set small, in operation S620.

Thereafter, the RGB image and the NIR image are fused together according to the alpha ('α') value in the manner given in Equations 5(a)-5(c), and thus, a final fused image is output. Equations 5(a)-5(c) suggest an example of the concept of adjusting fusion rates of an NIR image and an RGB image according to image characteristics. Thus, it should be noted that modifications may be made thereto.

The inventive concept may be embodied as a computer-readable code on a computer-readable recording medium. The computer-readable recording medium is any data storage device that can store data which can be thereafter read by a computer system. Examples of computer-readable recording media include read-only memory (ROM), random-access memory (RAM), CD-ROMs, magnetic tapes, floppy disks, optical data storage devices, etc. The computer-readable recording medium may also be distributed over network-coupled computer systems so that the computer-readable code is stored and executed in a decentralized fashion. Also, functional programs, code, and code segments for implementing the inventive concept can be easily construed by programmers of ordinary skill in the art.

While the inventive concept has been particularly shown and described with reference to exemplary embodiments thereof, it will be understood by one of ordinary skill in the art that various changes in form and detail may be made therein without departing from the spirit and scope of the inventive concept as defined by the following claims. Accordingly, the disclosed embodiments should be considered in a descriptive sense and not in a restrictive sense. The scope of the inventive concept will be defined by the appended claims, and differences in scope equivalent to the appended claims should be construed as being included in the inventive concept.

What is claimed is:

1. An image fusion apparatus using a multi-spectral filter array sensor, the image fusion apparatus comprising at least one processor to implement:
   a separation unit configured to separate an input image input through the multi-spectral filter array sensor into an RGB image and a near infrared (NIR) image;
   a color reconstruction unit configured to extract an RGB image in a visible band by removing an NIR value incident together with R, G and B values through the multi-spectral filter array sensor from the R, G and B values; and
   an image fusion unit configured to fuse the RGB image in the visible band with the NIR image, in which a fusion rate of the RGB image and the NIR image is based on a size of each of the R, G and B values of the RGB image in the visible band,
   wherein respective color channels R', G', and B' fused by the image fusion unit are given by:

$$\begin{pmatrix} R' \\ G' \\ B' \end{pmatrix} = \begin{pmatrix} 1+k & 0 & 0 \\ 0 & 1+k & 0 \\ 0 & 0 & 1+k \end{pmatrix} \cdot \begin{pmatrix} R \\ G \\ B \end{pmatrix},$$

where $$k = \frac{3N}{R+G+B},$$

and N indicates the NIR image.

2. The image fusion apparatus of claim 1, wherein the multi-spectral filter array sensor comprises a color filter which passes light components of the visible band ranging from 400 nm to 700 nm, such as RGB, and an NIR filter which passes light components of an NIR zone of 700 nm to 1100 nm in the invisible band.

3. The image fusion apparatus of claim 1, wherein the color reconstruction unit extracts the RGB image in the visible band by removing the NIR value from each of all band values of color channels comprising R, G and B channels of the RGB image.

4. The image fusion apparatus of claim 1, wherein a brightness of an image resulting from fusion by the image fusion unit is I' (Intensity)=(R'+G'+B')/3.

5. An image fusion apparatus using a multi-spectral filter array sensor, the image fusion apparatus comprising at least one processor to implement:
   a separation unit configured to separate an input image input through the multi-spectral filter array sensor into an RGB image and a near infrared (NIR) image;
   a color reconstruction unit configured to extract an RGB image in a visible band by removing an NIR value incident together with R, G and B values through the multi-spectral filter array sensor from the R, G and B values; and
   an image fusion unit configured to fuse the RGB image in the visible band with the NIR image, in which a fusion rate of the RGB image and the NIR image is based on a size of each of the R, G and B values of the RGB image in the visible band,
   wherein the image fusion unit is further configured to adjust the fusion rate according to local or global characteristics of the input image, and
   wherein respective color channels R', G', and B' fused by the image fusion unit are given by:

$$R'=N\times(1-\alpha)\times R/(R+G+B)+N\times\alpha$$

$$G'=N\times(1-\alpha)\times G/(R+G+B)+N\times\alpha$$

$$B'=N\times(1-\alpha)\times B/(R+G+B)+N\times\alpha,$$

where α is implemented to be changed according to the local or global characteristics of the input image.

6. The image fusion apparatus of claim 5, wherein the color reconstruction unit extracts the RGB image in the visible band by removing NIR values from each of all band values of color channels comprising R, G and B channels of the RGB image.

7. An image fusion method using a multi-spectral filter array sensor, the image fusion method comprising:
   extracting an RGB image in a visible band from an RGB image input through the multi-spectral filter array sensor;
   receiving input of an NIR image through an NIR filter of the multi-spectral filter array sensor;
   calculating a size of each of R, G and B values of the RGB image in the visible band; and
   fusing the RGB image in the visible band with the NIR image according to the calculated size of each of R, G, and B pixels, wherein respective color channels R', G', and B' fused in the fusing are given by:

$$\begin{pmatrix} R' \\ G' \\ B' \end{pmatrix} = \begin{pmatrix} 1+k & 0 & 0 \\ 0 & 1+k & 0 \\ 0 & 0 & 1+k \end{pmatrix} \cdot \begin{pmatrix} R \\ G \\ B \end{pmatrix},$$

where $$k = \frac{3N}{R+G+B},$$

and N indicates the NIR image.

8. The image fusion method of claim 7, wherein the multi-spectral filter array sensor is mounted on an image processing apparatus which comprises a surveillance camera.

9. The image fusion method of claim 7, wherein the extracting the RGB image in the visible band is performed by removing an NIR value incident together with R, G and B values through the multi-spectral filter array sensor from the R, G and B values.

10. The image fusion method of claim 9, wherein the removing the NIR value comprises removing the NIR value from each of all band values of color channels comprising R, G and B channels of the RGB image.

11. An image fusion method using a multi-spectral filter array sensor, the image fusion method comprising:
   extracting an RGB image in a visible band from an RGB image input through the multi-spectral filter array sensor;
   receiving input of an NIR image through an NIR filter of the multi-spectral filter array sensor;
   calculating a size of each of R, G and B values of the RGB image in the visible band; and
   fusing the RGB image in the visible band with the NIR image according to the calculated size of each of R, G, and B pixels,
   wherein in the fusing the RGB image in the visible band with the NIR image, a fusion rate of the two images is adjusted according to local or global characteristics of the input image, and
   wherein respective color channels R', G', and B' fused by the fusing the RGB image in the visible band with the NIR image are given by:

$$R' = N \times (1-\alpha) \times R/(R+G+B) + N \times \alpha$$

$$G' = N \times (1-\alpha) \times G/(R+G+B) + N \times \alpha$$

$$B' = N \times (1-\alpha) \times B/(R+G+B) + N \times \alpha,$$

where α is implemented to be changed according to the local or global characteristics of the input image.

* * * * *